(12) United States Patent
Fudoji et al.

(10) Patent No.: US 9,717,893 B2
(45) Date of Patent: Aug. 1, 2017

(54) MICRONEEDLE ARRAY

(71) Applicant: HISAMITSU PHARMACEUTICAL CO., INC., Tosu-shi, Saga (JP)

(72) Inventors: Ryusuke Fudoji, Tsukuba (JP); Makoto Ogura, Tsukuba (JP)

(73) Assignee: HISAMITSU PHARMACEUTICAL CO., LTD., Tosu-Shi, Saga (JP)

( * ) Notice: Subject to any disclaimer, the term of this patent is extended or adjusted under 35 U.S.C. 154(b) by 8 days.

(21) Appl. No.: 14/767,138

(22) PCT Filed: Feb. 12, 2014

(86) PCT No.: PCT/JP2014/053186
§ 371 (c)(1),
(2) Date: Aug. 11, 2015

(87) PCT Pub. No.: WO2014/126101
PCT Pub. Date: Aug. 21, 2014

(65) Prior Publication Data
US 2015/0374967 A1 Dec. 31, 2015

(30) Foreign Application Priority Data
Feb. 13, 2013 (JP) ................................ 2013-025586

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01); *A61M 2037/0061* (2013.01)

(58) Field of Classification Search
CPC .. A61M 2037/0023; A61M 2037/0061; A61M 37/0015
(Continued)

(56) References Cited

U.S. PATENT DOCUMENTS

| 6,743,211 B1 | 6/2004 | Prausnitz et al. |
| 7,087,035 B2 | 8/2006 | Trautman et al. |

(Continued)

FOREIGN PATENT DOCUMENTS

| EP | 1086718 A1 | 3/2001 |
| JP | 2001525231 A | 12/2001 |

(Continued)

OTHER PUBLICATIONS

International Application No. PCT/JP2014/053186, International Search Report dated Apr. 22, 2014, two (2) pages.

(Continued)

*Primary Examiner* — Kevin C Sirmons
*Assistant Examiner* — Deanna K Hall
(74) *Attorney, Agent, or Firm* — Nath, Goldberg & Meyer; Joshua B. Goldberg; Tanya E. Harkins

(57) ABSTRACT

A microneedle array in accordance with one embodiment comprises at least a first microneedle and a second microneedle that are inclined with respect to a support face. A tip of the first microneedle points in a first direction, and a tip of the second microneedle points in a second direction different from the first direction. The first microneedle in contact with skin is stuck into the skin while being moved along a surface of the skin in the first direction. The second microneedle in contact with the skin is stuck into the skin while being moved along the surface of the skin in the second direction.

7 Claims, 21 Drawing Sheets

(58) Field of Classification Search
USPC .......................................................... 604/173
See application file for complete search history.

(56) References Cited

U.S. PATENT DOCUMENTS

| | | |
|---|---|---|
| 2002/0032415 A1 | 3/2002 | Trautman et al. |
| 2004/0087992 A1 | 5/2004 | Gartstein et al. |
| 2008/0103434 A1* | 5/2008 | Lastovich ............ A61B 17/205 |
| | | 604/46 |
| 2011/0237925 A1 | 9/2011 | Yue et al. |

FOREIGN PATENT DOCUMENTS

| | | |
|---|---|---|
| JP | 2002510982 A | 4/2002 |
| JP | 2003534881 A | 11/2003 |
| JP | 2012055343 A | 3/2012 |
| KR | 20120041487 A | 5/2012 |
| WO | 2006116281 A2 | 11/2006 |

OTHER PUBLICATIONS

International Application No. PCT/JP2014/053186, International Preliminary Report of Patentability dated Aug. 27, 2015, eight (8) pages.
Supplementary European Search Report dated Sep. 13, 2016 corresponding to European application No. EP14751051.

* cited by examiner

MICRONEEDLE ARRAY

This is a National Phase Application filed under 35 U.S.C. 371 as a national stage of PCT/JP2014/053186, filed Feb. 12, 2014, an application claiming the benefit of Japanese Application No. P2013-025586, filed Feb. 13, 2013, the content of each of which is hereby incorporated by reference in its entirety.

TECHNICAL FIELD

One aspect of the present invention relates to a microneedle array

BACKGROUND ART

Conventionally, there are known a microneedle that administers an active ingredient through skin and a device provided with the microneedle. For example, Patent Literature 1 below describes a device provided with micro-stingers generated by punching a surface of a thin sheet with a series of protrusions. Patent Literature 2 below describes a device that includes a sheet member provided with a plurality of micro-protrusions.

There is also known a technique in which skin is stretched to be punctured with a microneedle. For example, Patent Literature 3 below describes a fact that a positioned device is pressed downward on skin and a stretching device stretches the skin in a target area of a skin penetration member to enable uniform penetration through the skin. In addition, Patent Literature 4 below describes a fact that two internal expansion sections are moved so as to move away from each other to allow skin to be stuck with micro-protrusions while stretching the skin and then the expansion sections are moved to allow the micro-protrusions to cut the skin. Further, Patent Literature 5 below describes a technique in which extendable pyramids are pressed on skin to stretch the skin so that a microneedle arranged in each of the pyramids is punctured into the skin.

CITATION LIST

Patent Literature

[Patent Literature 1] JP 2002-510982 A
[Patent Literature 2] JP 2001-525231 A
[Patent Literature 3] JP 2003-534881 A
[Patent Literature 4] U.S. Pat. No. 7,087,035 B
[Patent Literature 5] U.S. Pat. No. 6,743,211 B

SUMMARY OF INVENTION

Technical Problem

If skin is deformed before being punctured, a further member or mechanism is required to achieve the deformation. As a result, a device necessarily increases in size. Thus, it is required to downsize a device for achieving puncture along with deformation of skin.

Solution to Problem

A microneedle array in accordance with one aspect of the present invention comprises at least a first microneedle and a second microneedle that are inclined with respect to a support face, and in the microneedle array, a tip of the first microneedle points in a first direction and a tip of the second microneedle points in a second direction different from the first direction, the first microneedle in contact with skin is stuck into the skin while moving in the first direction along a surface of the skin, and the second microneedle in contact with the skin is stuck into the skin while moving in the second direction along the surface of the skin.

According to this aspect, since each of the first and second microneedles pointing in a different direction is moved along a tip direction of each of the microneedles, a direction of movement is different between a portion in contact with the first microneedle and a portion in contact with the second microneedle. The difference in the direction of movement causes deformation of skin, so that the microneedles are to be stuck into the deformed skin. In this way, since the microneedles themselves deform the skin, another member or mechanism for achieving the deformation is unnecessary, whereby it is possible to reduce a puncture device in size accordingly.

In the microneedle array in accordance with another aspect, each of the first microneedle and the second microneedle may be stuck into the skin while rotationally moved.

In the microneedle array in accordance with yet another aspect, there are provided a first line including at least one first microneedle and a second line including at least one second microneedle, and the first line and the second line may extend radially.

In the microneedle array in accordance with yet another aspect, each of the first line and the second line may be arranged along an arc.

In the microneedle array in accordance with yet another aspect, a microneedle positioned in a center portion of the support face may be longer than a microneedle positioned in a peripheral portion of the support face.

In the microneedle array in accordance with yet another aspect, a microneedle positioned in the center portion of the support face may be shorter than a microneedle positioned in the peripheral portion of the support face.

In the microneedle array in accordance with yet another aspect, an inclination angle of a microneedle positioned in the center portion of the support face may be larger than that of a microneedle positioned in the peripheral portion of the support face.

In the microneedle array in accordance with yet another aspect, the support face includes a first support face and a second support face positioned outside the first support face, and after a microneedle positioned in the first support face starts to be rotationally moved, a microneedle positioned in the second support face may start to be rotationally moved.

In the microneedle array in accordance with yet another aspect, the support face may be convex.

In the microneedle array in accordance with yet another aspect, the first microneedle is provided in the first support face and the second microneedle is provided in the second support face independent of the first support face, and the first support face may be moved in the first direction and the second support face may be moved in the second direction.

In the microneedle array in accordance with yet another aspect, the first support face and the second support face may be moved parallel to themselves.

Advantageous Effects of Invention

According to the one aspect of the present invention, it is possible to downsize a device for achieving puncture along with deformation of skin.

DESCRIPTION OF EMBODIMENTS

Figure 1:
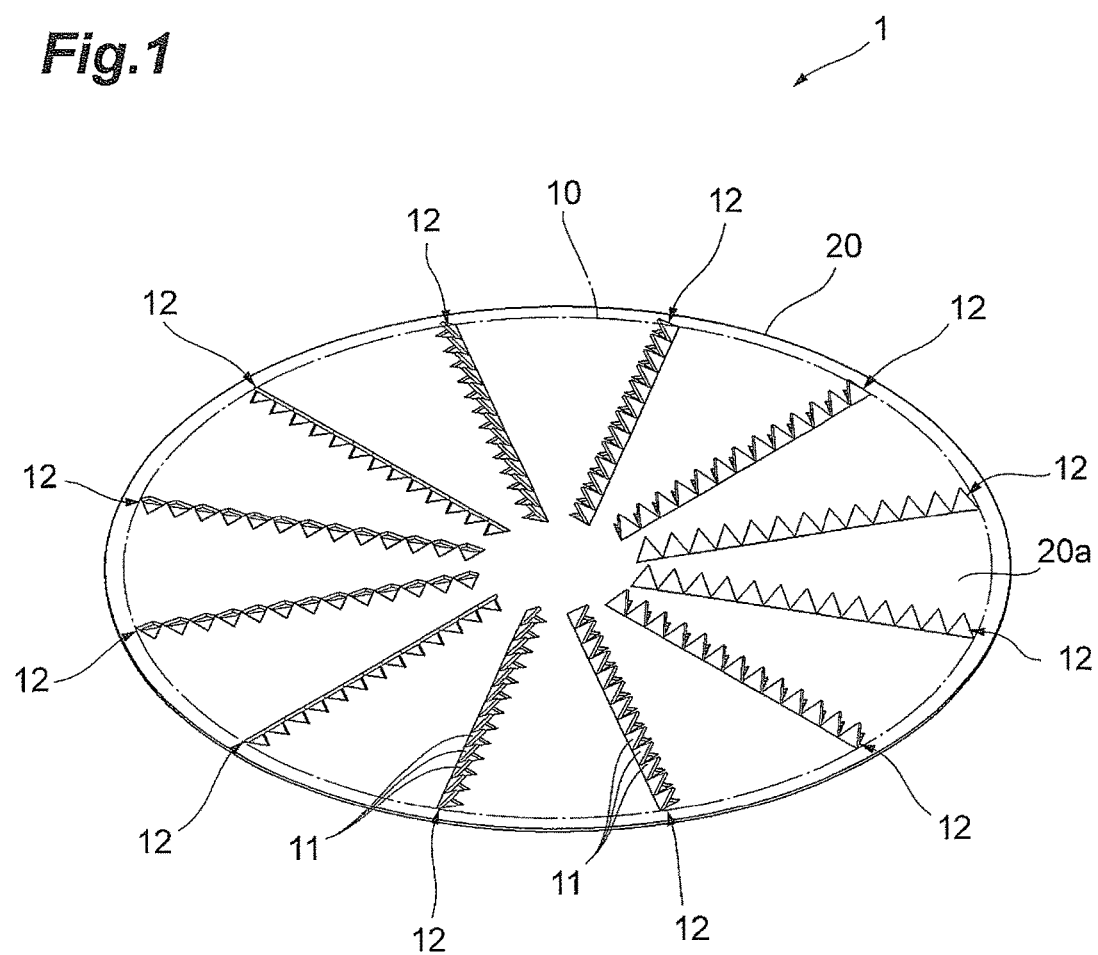
FIG. 1 is a perspective view of a microneedle device in accordance with a first embodiment.

Hereinafter, the embodiments of the present invention are described with reference to accompanying drawings. In description of the drawings, the same or similar element is designated by the same reference numeral without duplicated description on the element.

First Embodiment

With reference to FIGS. 1 to 5, a structure of a microneedle array 10 in accordance with the first embodiment will be described. The microneedle array 10 is a set of a plurality of microneedles 11 to be stuck into skin, and is arranged on an arbitrary support face. In the present embodiment, the microneedle array 10 is a part of a sheet-like microneedle device 1.

Figure 4:
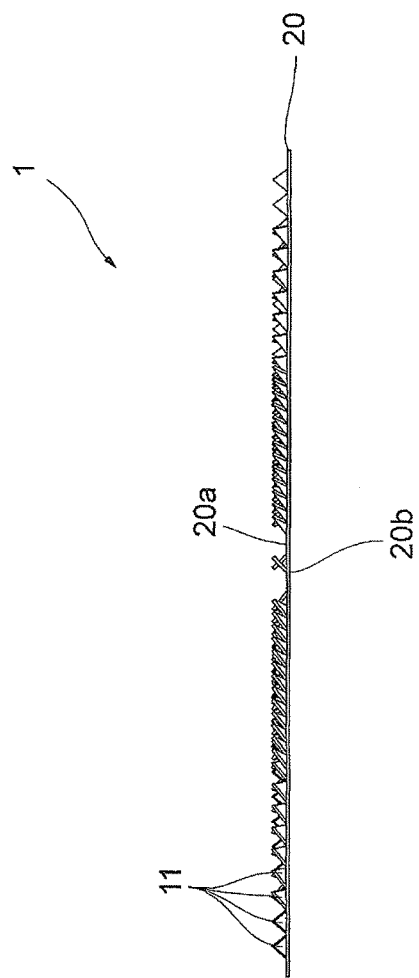
FIG. 4 is a side view of the microneedle device shown in FIG. 1.

The microneedle device 1 is a tool for transdermally administering an active ingredient by puncturing skin. The microneedle device 1 is completed by cutting a circular sheet 20 to form a large number of microneedles 11 and by erecting the microneedles 11 in an oblique direction from a sheet face. As shown in FIG. 4, all of the microneedles 11 are erected on a principal face (support face) 20a. Any acute angle is applicable to an angle (or an inclination angle) between each of the microneedles 11 and the principal face 20a. The principal face 20a faces skin when the microneedle device 1 is used. A back face 20b of the sheet 20 is the back of the principal face 20a, and a finger or any auxiliary tool touches the back face 20b for puncture when the microneedle device 1 is used.

Material of the sheet 20 and the microneedles 11 is not limited. For example, the sheet 20 and the microneedles 11 may be made from any one of stainless steel, polyethylene terephthalate (PET), another metal, another resin, biodegradable material, ceramic, and bioabsorbable material. Alternatively, the sheet 20 and the microneedles 11 may be made from a combination of the materials.

It is possible to form the microneedle array 10 by etching. If a sheet is metal, it is possible to form the microneedle array 10 by etching the sheet with a chemical solution to form a large number of microneedles 11 and by erecting the microneedles 11 in an oblique direction. If a sheet is non-metal, the sheet may be cut with a laser to form a large number of microneedles 11, and the microneedles 11 may be erected as with the case of a metal sheet. If etching is used as above, a void is generated around each of the microneedles 11. As a matter of course, the microneedle array 10 may be formed by any method other than etching.

Dimensions of the sheet 20 are not limited, and may be optionally set depending on an intended purpose or a usage portion. For example, a lower limit of a diameter of the sheet 20 is determined in consideration of a dose of an active ingredient, and an upper limit of the diameter is determined in consideration of a size of a biological body. For example, the lower limit of the diameter may be 0.1 cm or 1 cm, and the upper limit of the diameter may be 60 cm, 50 cm, 30 cm or 20 cm. In the present embodiment, since the microneedles 11 are formed by cutting the sheet 20, the thickness of the sheet 20 is determined in consideration of puncture performance of the microneedles 11. For example, a lower limit of the thickness may be 5 μm or 20 μm, and an upper limit of the thickness may be 1000 μm or 300 μm.

Parameters related to the microneedle 11 are also not limited. For example, a lower limit of the length of the microneedle 11 may be 10 μm or 100 μm, and an upper limit of the length may be 10000 μm or 1000 μm. Here, the length of the microneedle 11 is a distance from the base (a root of a portion erected from the principal face 20a) of the microneedle 11 to an apex thereof. As described above, in the present embodiment, the thickness of the microneedle 11 depends on the thickness of the sheet 20. A lower limit of density of the microneedle 11 may be 0.05 piece/cm$^2$ or 1 piece/cm$^2$, and an upper limit of the density may be 10000 pieces/cm$^2$, or 5000 pieces/cm$^2$. The lower limit of the density is a value calculated in terms of the number of needles and area thereof capable of administering 1 mg of an active ingredient, and the upper limit of the density is a limit value in consideration of a shape of the needle.

Figure 2:
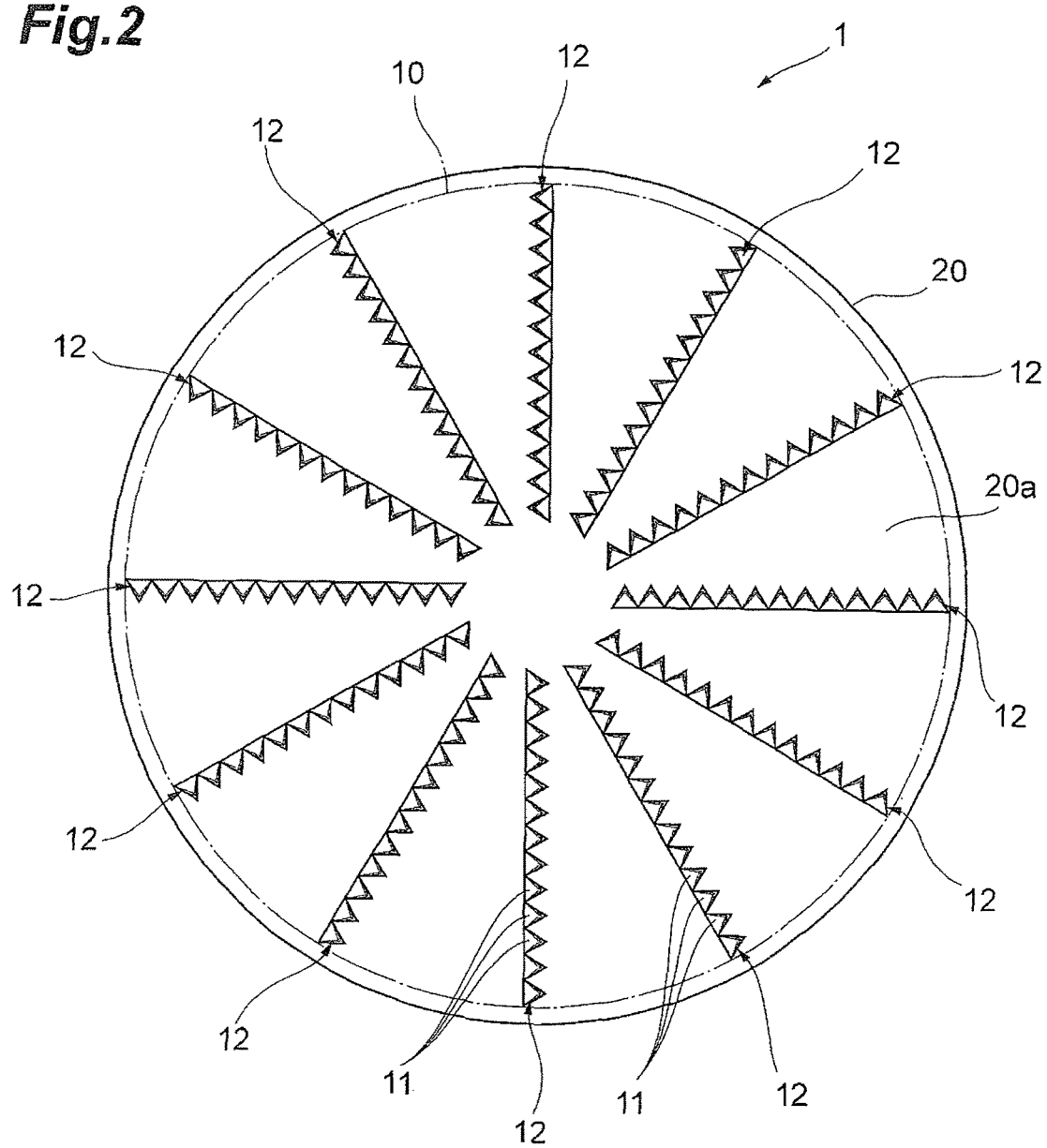
FIG. 2 is a plan view of the microneedle device shown in FIG. 1.
Figure 3:
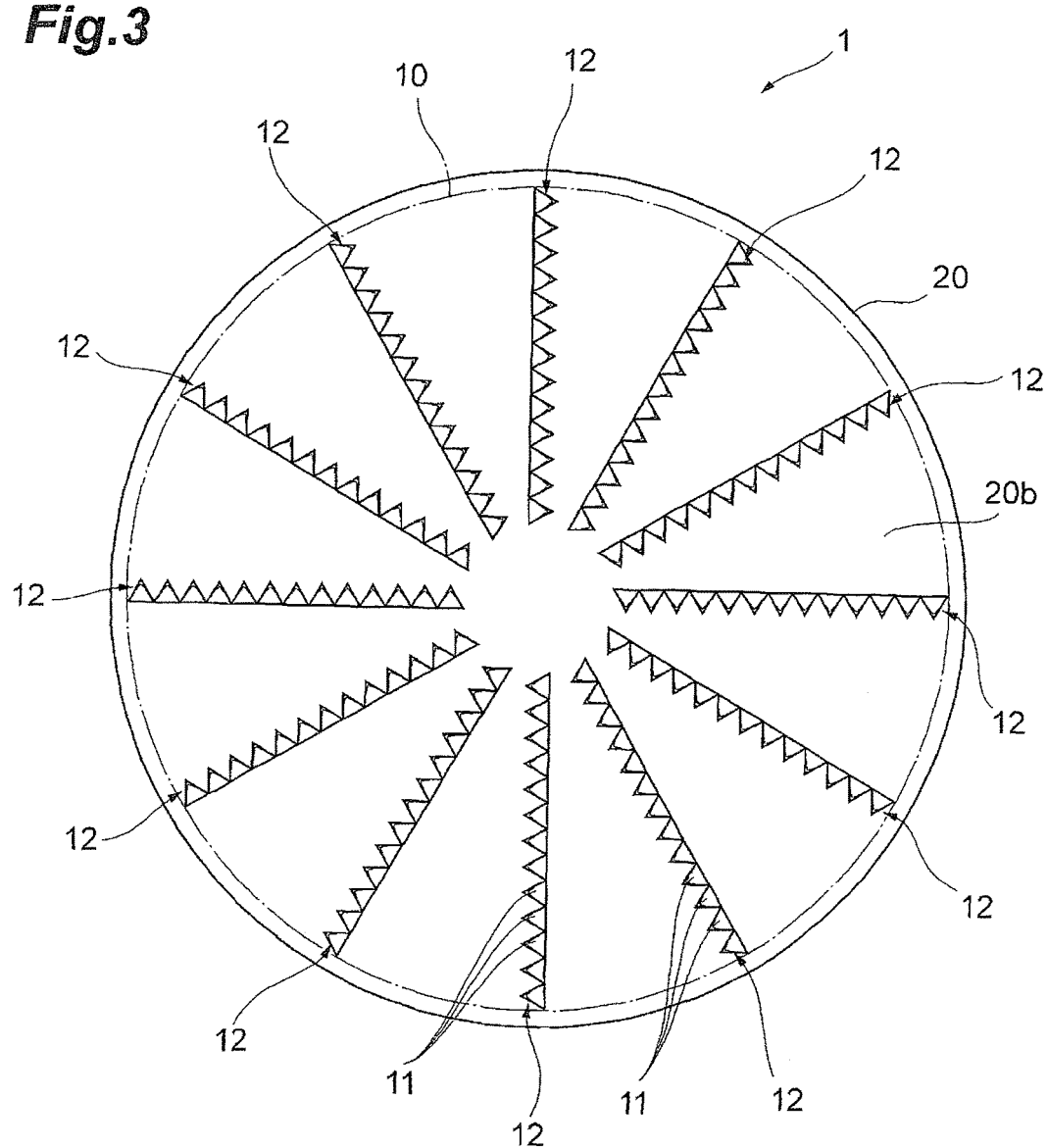
FIG. 3 is a bottom view of the microneedle device shown in FIG. 1.

As shown in FIGS. 1 to 3, the microneedle array 10 is a set of a plurality of lines 12 each of which extends along a radial direction of the sheet 20. Each of the lines 12 is composed of the plurality of microneedles 11. The plurality of lines 12 extends radially from near the center of the sheet 20. In the present embodiment, although every angle between two lines adjacent to each other is 30°, the angle is not limited. For example, the angle may be 10°, 15°, 45°, 60°, 90°, 120°, or 180°. In addition, the angle may not be uniform.

Figure 5:
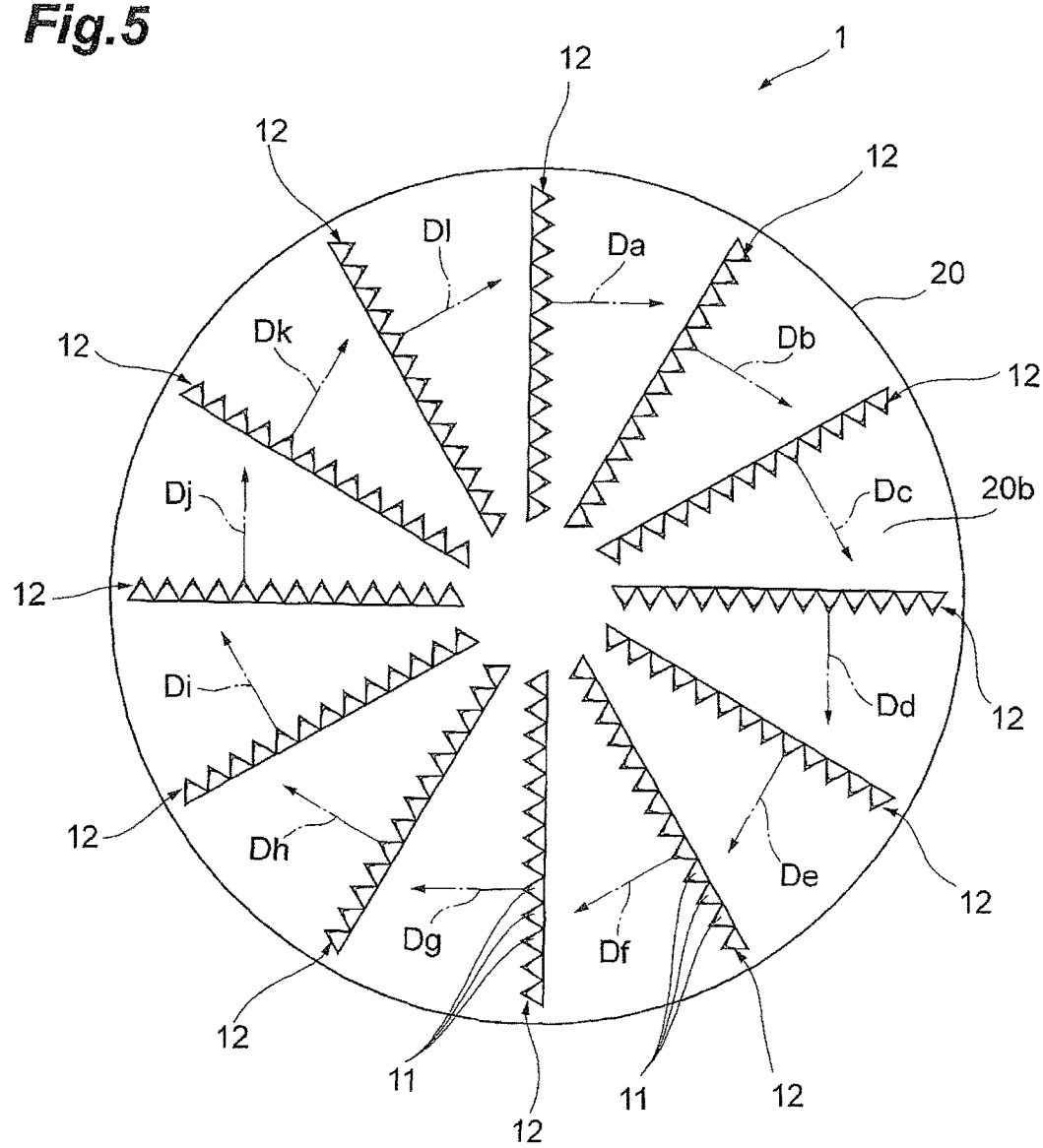
FIG. 5 shows directions of tips of microneedles shown in FIG. 1

When the whole of the microneedle array 10 is viewed, directions in which all of the microneedles 11 point are unified into a clockwise direction or a counterclockwise direction. In the present embodiment, when the microneedle device 1 is viewed from the back face 20b, the microneedle array 10 points in the clockwise direction as a whole. All tips of the plurality of microneedles 11 in one line 12 point in the same direction. Each of arrows Da to Dl shown in FIG. 5 shows a tip direction of the microneedles 11 of each of the lines 12. As can be seen from the arrows, with respect to any two lines, a direction (first direction) in which a tip of each of the microneedles (first microneedles) 11 in one line (first line) 12 points is different from a direction (second direction) in which a tip of each of the microneedles (second microneedles) 11 in the other line (second line) 12 points. There may be at least one pair of two lines in which a tip direction of the microneedles 11 is different from each other, and thus, with respect to a specific plurality of lines, a tip direction of the microneedles 11 may be the same.

The length of the microneedles 11 in the microneedle array 10 may not be uniform. For example, the microneedle 11 positioned in a center portion of the sheet 20 may be longer than the microneedle 11 positioned in a peripheral portion of the sheet 20. As a further variation of this type, in each of the lines 12, each of the microneedles 11 may be formed so that the microneedle 11 gradually increases in length from the peripheral portion of the sheet 20 to the center portion thereof. Alternatively, the microneedle 11 positioned in the center portion of the sheet 20 may be shorter than the microneedle 11 positioned in the peripheral portion of the sheet 20. As a further variation of this type, in each of the lines 12, each of the microneedles 11 may be formed so that the microneedle 11 gradually decreases in length from the peripheral portion of the sheet 20 to the center portion thereof.

In the microneedle array 10, an angle (or an inclination angle) between the microneedle 11 and the principal face 20a may not be uniform. For example, the microneedle 11 positioned in the center portion of the sheet 20 may have an inclination angle larger than that of the microneedle 11 positioned in the peripheral portion of the sheet 20. As a further variation of this type, in each of the lines 12, each of the microneedles 11 may be formed so that the inclination angle of the microneedle 11 gradually increases from the peripheral portion of the sheet 20 to the center portion thereof. If the length of each of the microneedles 11 is allowed to be different as described above, an inclination angle of each of the microneedles 11 may be set so that height of each of the microneedles 11 is the same or almost the same. Here, the height of the microneedle 11 is a distance from the principal face 20a to the apex of the microneedle 11.

In the microneedle array 10, both of a length and an inclination angle of the microneedle 11 may not be uniform. For example, a length and an inclination angle of the microneedle 11 positioned in the center portion of the sheet 20 is larger than those of the microneedle 11 positioned in the peripheral portion of the sheet 20. As a further variation of this type, in each of the lines 12, each of the microneedles 11 may be formed so that the length and the inclination angle of the microneedle 11 gradually increase from the peripheral portion of the sheet 20 to the center portion thereof. Alternatively, the microneedle 11 positioned in the center portion of the sheet 20 may have a length shorter as well as an inclination angle larger than those of the microneedle 11 positioned in the peripheral portion of the sheet 20. As a further variation of this type, in each of the lines 12, each of the microneedles 11 may be formed so that the inclination angle of the microneedle 11 gradually increases from the peripheral portion of the sheet 20 to the center portion thereof while the length thereof decreases.

As with the example described above, a length or an inclination angle between the microneedle 11 in the peripheral portion of the sheet 20 and the microneedle 11 in the center portion of the sheet 20 is changed to allow the microneedle 11 positioned in the center portion of the sheet 20 to be reliably stuck into skin.

A tip of each of the microneedles 11 may point in a tangential direction of a virtual circle, which shows a turning direction of the microneedles 11. The example shown in FIGS. 2 and 3 is one aspect of that type. Alternatively, the tip of each of the microneedles 11 may point in a direction that is closer to the center of the sheet 20 than the tangential direction. In this case, it is possible to reduce resistance to be applied to each of the microneedles 11 at the time of puncture.

Next, with reference to FIGS. 6 to 10, a method of use of the microneedle device 1 will be described.

A preparation method of an active ingredient at the time of using the microneedle device 1 is not limited. For example, the following is considered as the preparation method: a method of applying coating of an active ingredient to the microneedle device 1 itself in advance; a method of applying an active ingredient to skin before the microneedle device 1 is placed on the skin; and a method of applying an active ingredient to skin after the microneedle device 1 is punctured into the skin. The coating may be performed by using a principle of screen printing or by another method. In a case where a biodegradable sheet is used, it is possible to allow the sheet itself to contain an active ingredient. Alternatively, a reservoir or a gel, containing the active ingredient, may be provided on the back face 20b. In addition, after or during puncture, a medication may be delivered intradermally by using energy, such as spring, pressure, electricity, and magnetism.

Figure 6:
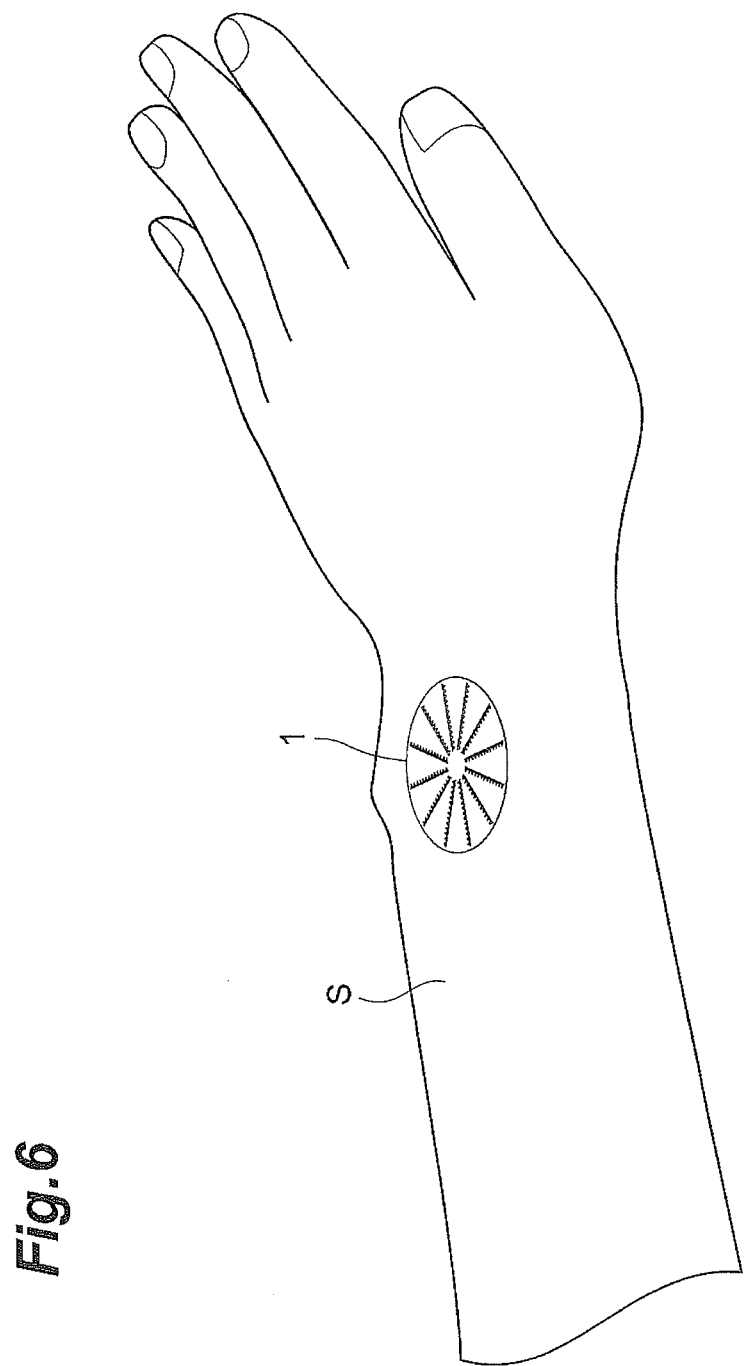
FIG. 6 shows a state where the microneedle device is placed on skin.
Figure 7:
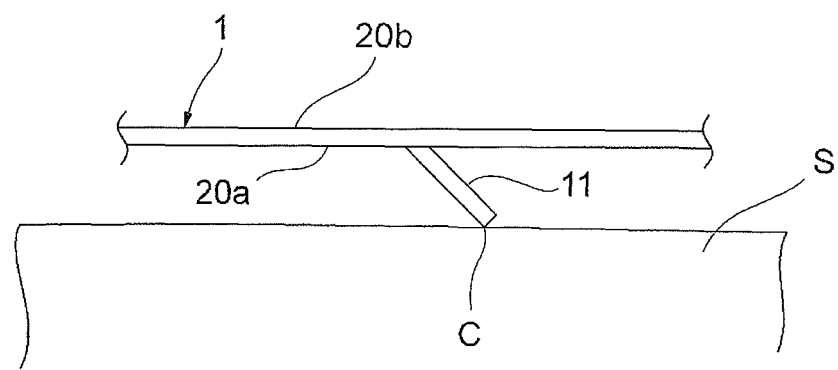
FIG. 7 schematically shows a state where a microneedle is in contact with skin.

First, while pointing the principal face 20a to skin S, a user places the microneedle device 1 on the skin to bring a tip of each of the microneedles 11 into contact with the skin S as shown in FIGS. 6 and 7. Hereinafter, a point at which the microneedle 11 is in contact with the skin S is referred to as a "contact point".

Figure 8:
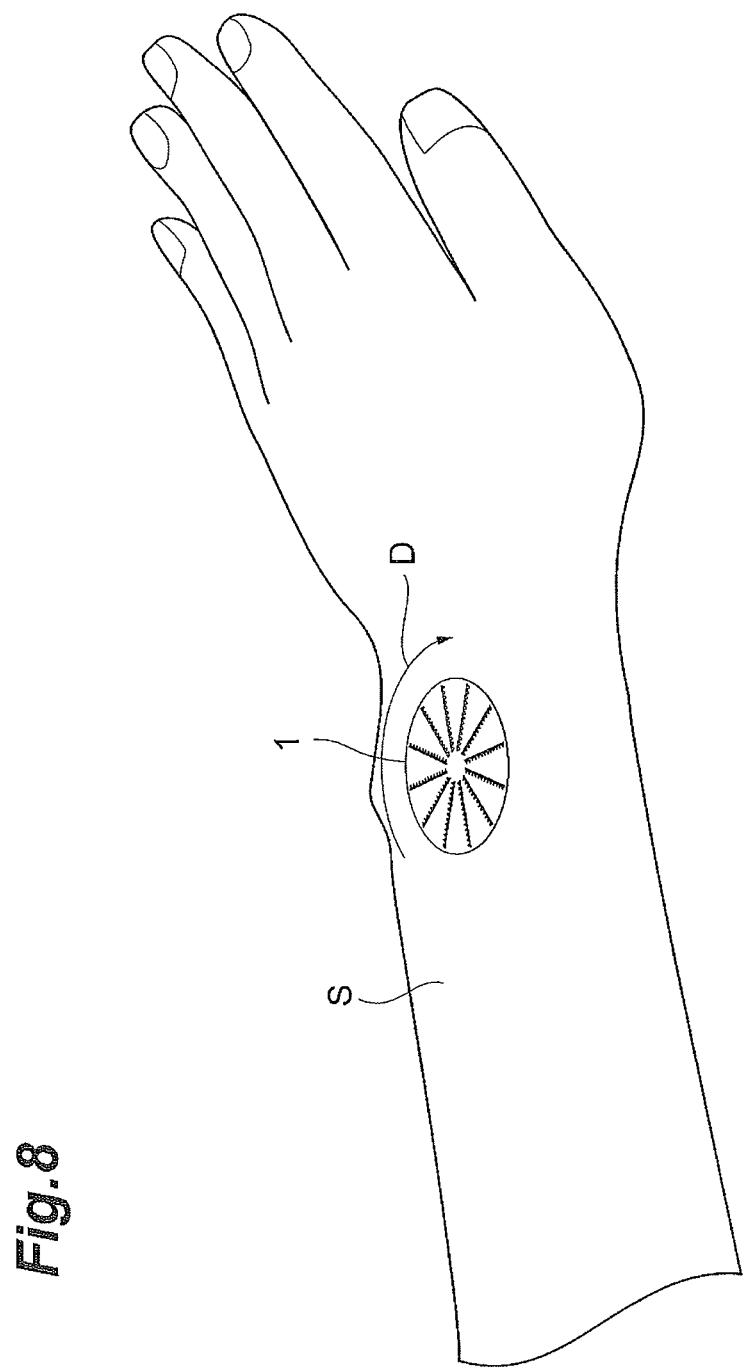
FIG. 8 shows a case of turning the microneedle device placed on skin.
Figure 9:
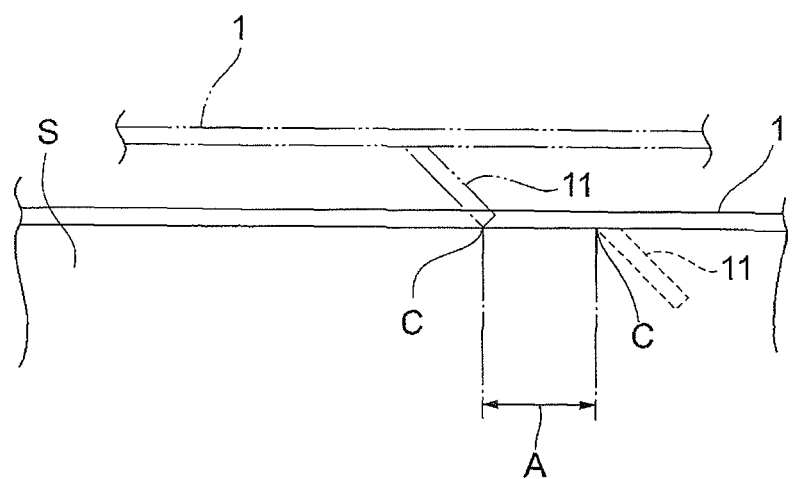
FIG. 9 schematically shows a state where the microneedle is stuck into skin.

Subsequently, as shown in FIG. 8, the user presses the back face 20b to press the microneedle device 1 into the skin while turning the microneedle device 1 in a direction D in which the tip of the microneedle 11 points. The turning and pressing allow each of the microneedles 11 to be stuck into the skin S from a contact point C as shown in FIG. 9 while turning along a surface of the skin S. At this time, the contact point C is displaced by a distance A as shown in FIG. 9, and this means that the skin S in the periphery of the contact point C is stretched or shrunk. Thus, it can be said that each of the microneedles 11 is stuck into the skin S while deforming the skin S by itself.

The user twists the microneedle device 1 in this manner to enable an active ingredient to be administered into one's own body. Thus, the microneedle device 1 can be referred to as a torsion type microneedle device. In addition, instead of removing the microneedle device 1 from the skin immediately after puncture, the user may continue to press the microneedle device 1 by hand or with an auxiliary tool such as a tape for a prescribed time with the state of puncturing maintained.

Figure 10:
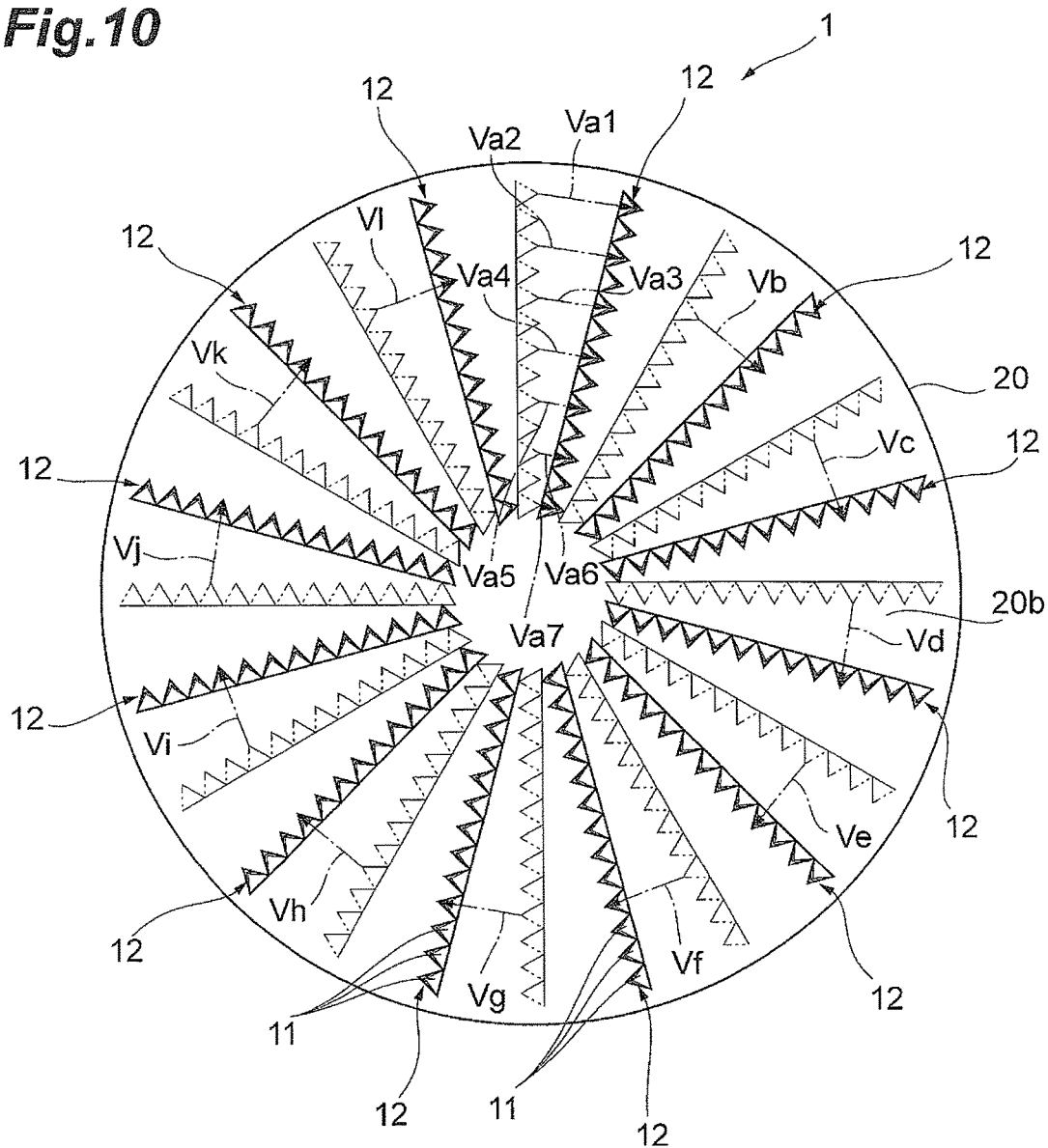
FIG. 10 shows turn of the microneedle device.

Since each of the lines 12 extending radially is arranged in the sheet 20 away from each other by a predetermined angle, a direction of movement of the microneedle 11 at the time of turning the microneedle device 1 is different for each of the lines 12. The difference is obvious because directions of motion vectors Va1, and Vb to V1 of the respective lines 12 in FIG. 10 are different. In addition, since the sheet 20 is turned, a distance of movement of each of the microneedles 11 in one line 12 is different from each other. The difference is obvious because the length of a motion vector of each of the microneedles 11 (in FIG. 10, only motion vectors Va1 to Va1 are shown) in one line 12 in FIG. 10 is different, for example. In this way, since a direction or distance of movement is different for each contact point C, skin in an area where the microneedle device 1 is applied is partially stretched or partially shrunk. In any case, when the microneedle device 1 is applied to skin, the skin in an application area thereof is deformed as a whole by each of the microneedles 11.

As described above, according to the present embodiment, since each of the microneedles 11 pointing a different direction is moved along a tip direction of each of the microneedles 11, a direction of movement of the microneedle 11 is different between a portion with which the microneedle 11 in one line 12 is in contact and a portion with which the microneedle 11 in another line 12 is in contact. In addition, since the microneedle device 1 in a circular shape is turned to perform puncture, a distance of movement of each of the microneedles 11 in one line 12 extending along a radial direction of the microneedle device 1 is different from each other. This kind of difference in a direction or distance causes skin to be deformed, so that the microneedles 11 are stuck into the skin deformed. In this way, since the microneedles 11 themselves deform the skin, another member or mechanism for achieving the deformation is unnecessary, whereby it is possible to reduce a puncture device in size accordingly.

Second Embodiment

With reference to FIGS. 11 to 15, a structure of a microneedle array 30 in accordance with a second embodiment will be described. In the present embodiment, the microneedle array 30 is a part of a sheet-like microneedle device 2. Hereinafter, a matter different from that of the first embodiment will be described in particular.

As shown in FIGS. 11 to 15, a microneedle device 2 in the present embodiment comprises a set of two rectangular sheets 40a and 40b. Since a principal face of a sheet 40a corresponds to the first support face and a principal face of a sheet 40b corresponds to the second support face, these two principal faces (support faces) are independent of each other.

Each of the sheets 40a and 40b comprises a large number of microneedles 11 formed by a method as with the first embodiment. The microneedle array 30 in the present embodiment is a set of a plurality of microneedles 11a on the sheet 40a and a plurality of microneedles 11b on the sheet 40b. In each of the sheets 40a and 40b, all of the microneedles 11 arranged in two dimensions point in the same direction. However, when the microneedle device 2 is used, the microneedles (first microneedles) 11a and the microneedles (second microneedles) 11b point in a different direction from each other.

Dimensions of each of the sheets 40a and 40b are not limited, and may be optionally set depending on an intended purpose or a usage portion. The dimensions of each of the two sheets 40a and 40b may be unified or may be different from each other. Even in the present embodiment, a lower limit of the length and the width of the sheets 40a and 40b is determined in consideration of a dose of an active ingredient, and an upper limit of the length and the width can be determined in consideration of a size of a biological body. In addition, it is possible to determine the thickness of the sheets 40a and 40b, and a size and density of the microneedles 11, as with the first embodiment.

With respect to a position relationship between the sheet 40a and the sheet 40b, various aspects can be thought in consideration of a direction (slide direction) of movement of each of the two sheets 40a and 40b.

Figure 11:
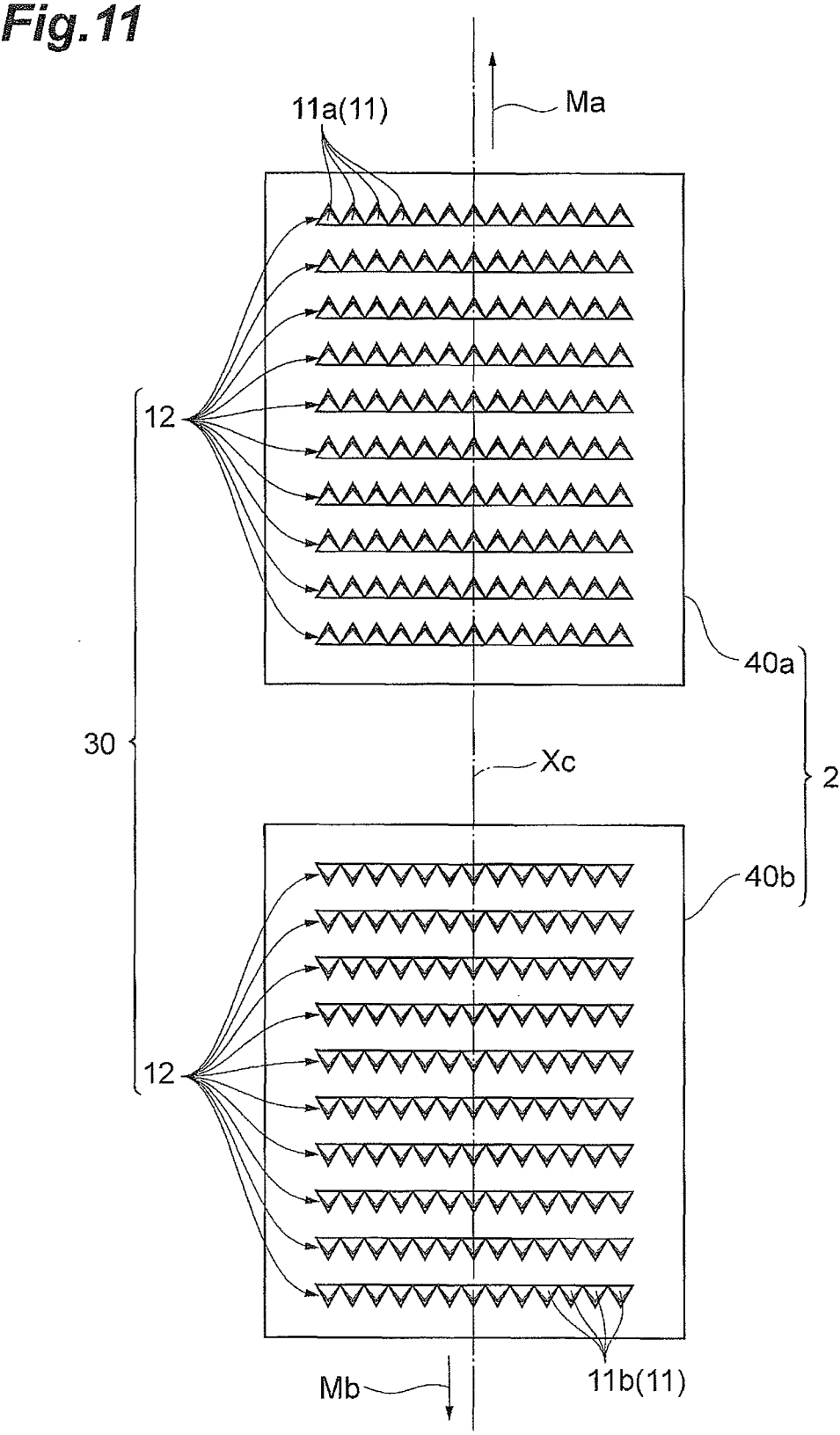
FIG. 11 is a plan view of one aspect of a microneedle device in accordance with a second embodiment.

In an example shown in FIG. 11, the sheets 40a and 40b are arranged so that the microneedles 11a and the microneedles 11b are arranged back to back. That is, a direction Ma of a tip of each of the microneedles 11a and a direction Mb of a tip of each of the microneedles 11b are different from each other by 180 degrees. Since each of the sheets 40a and 40b is moved along a tip direction of the microneedle 11, the direction Ma is also a direction of movement of the sheet 40a as well as the direction Mb is also a direction of movement of the sheet 40b. In this example, each of the two sheets 40a and 40b are arranged in juxtaposition to each other along one common axis Xc, and are moved along the axis Xc in the directions Ma and Mb, respectively. Thus, the sheets 40a and 40b move away from each other with the movement.

Figure 12:
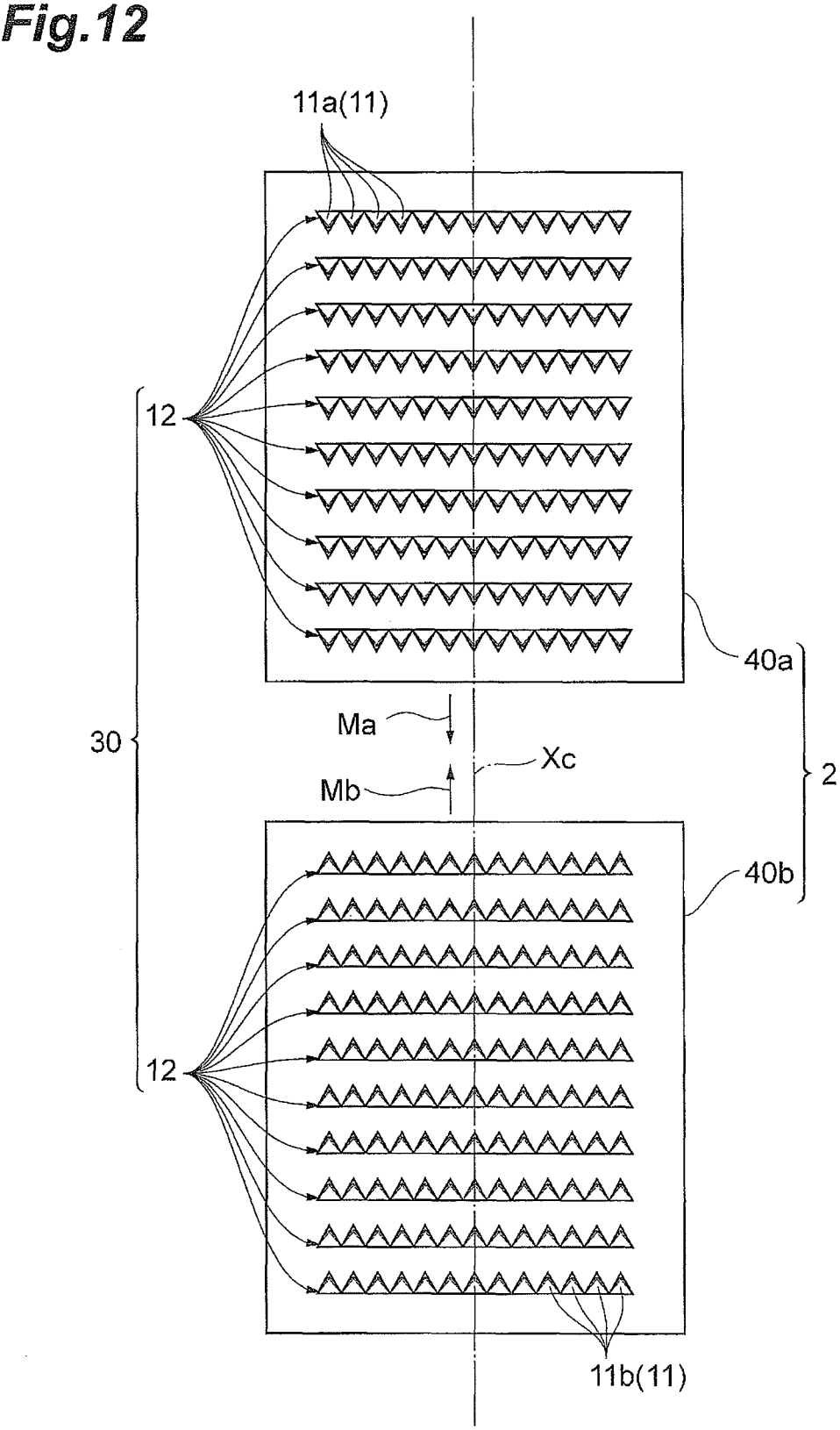
FIG. 12 is a plan view of another aspect of the microneedle device in accordance with the second embodiment.

In an example shown in FIG. 12, the sheets 40a and 40b are arranged so that the microneedles 11a and the microneedles 11b face each other. That is, a direction Ma of a tip of each of the microneedles 11a (a direction of movement of the sheet 40a) and a direction Mb of a tip of each of the microneedles 11b (a direction of movement of the sheet 40b) are different from each other by 180 degrees. In this example, each of the two sheets 40a and 40b are arranged in juxtaposition to each other along one common axis Xc, and are moved along the axis Xc in the directions Ma and Mb, respectively. Thus, the sheets 40a and 40b approach to each other with the movement.

Figure 13:
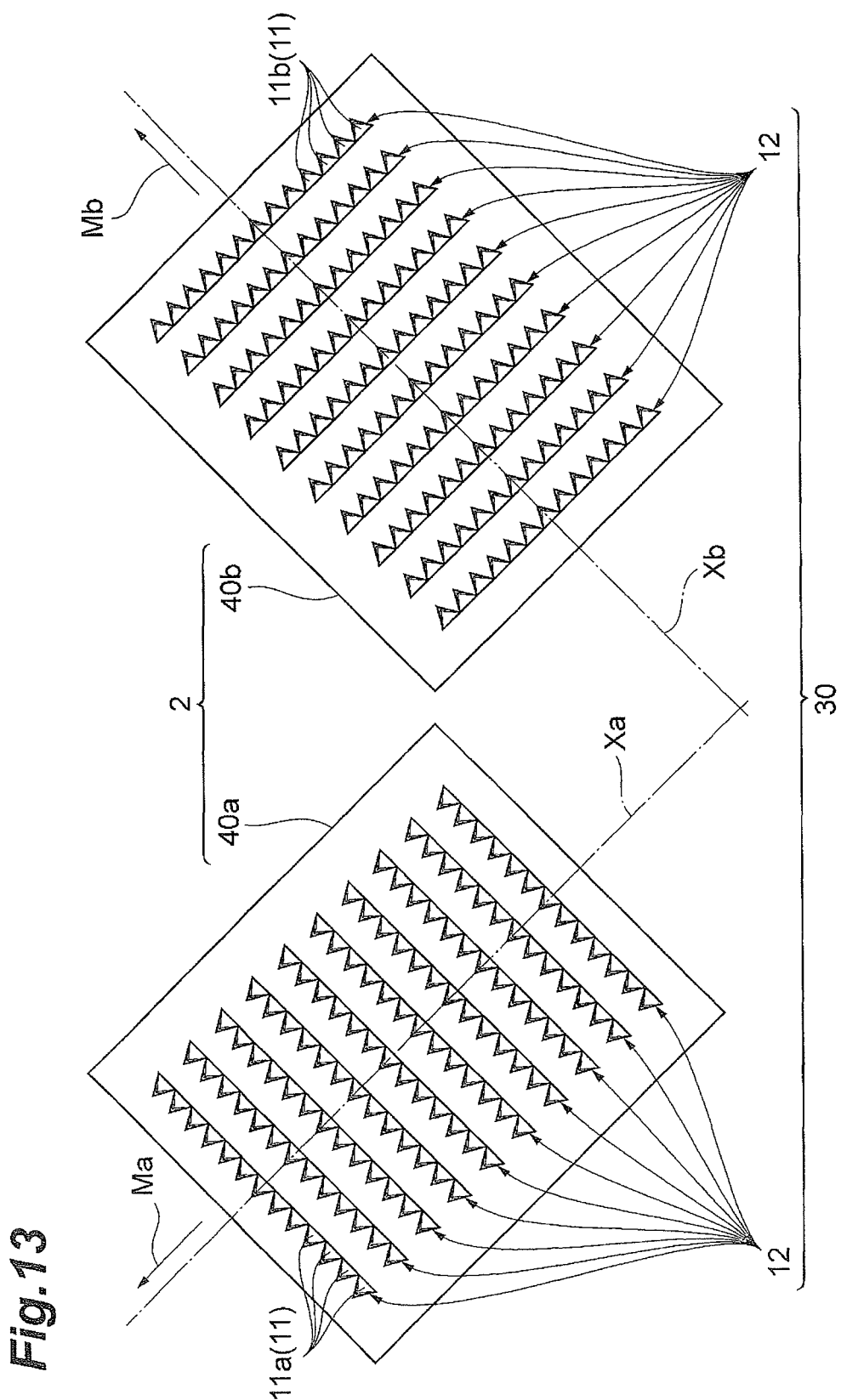
FIG. 13 is a plan view of yet another aspect of the microneedle device in accordance with the second embodiment.

In an example shown in FIG. 13, the sheets 40a and 40b are arranged so that an axis Xa along a tip direction Ma of each of the microneedles 11a and an axis Xb along a tip direction Mb of each of the microneedles 11b intersect each other. An angle between the two movement axes Xa and Xb is more than 0° and less than 180°. In this example, the two sheets 40a and 40b are moved so that the sheet 40a and the sheet 40b move away from each other.

Figure 14:
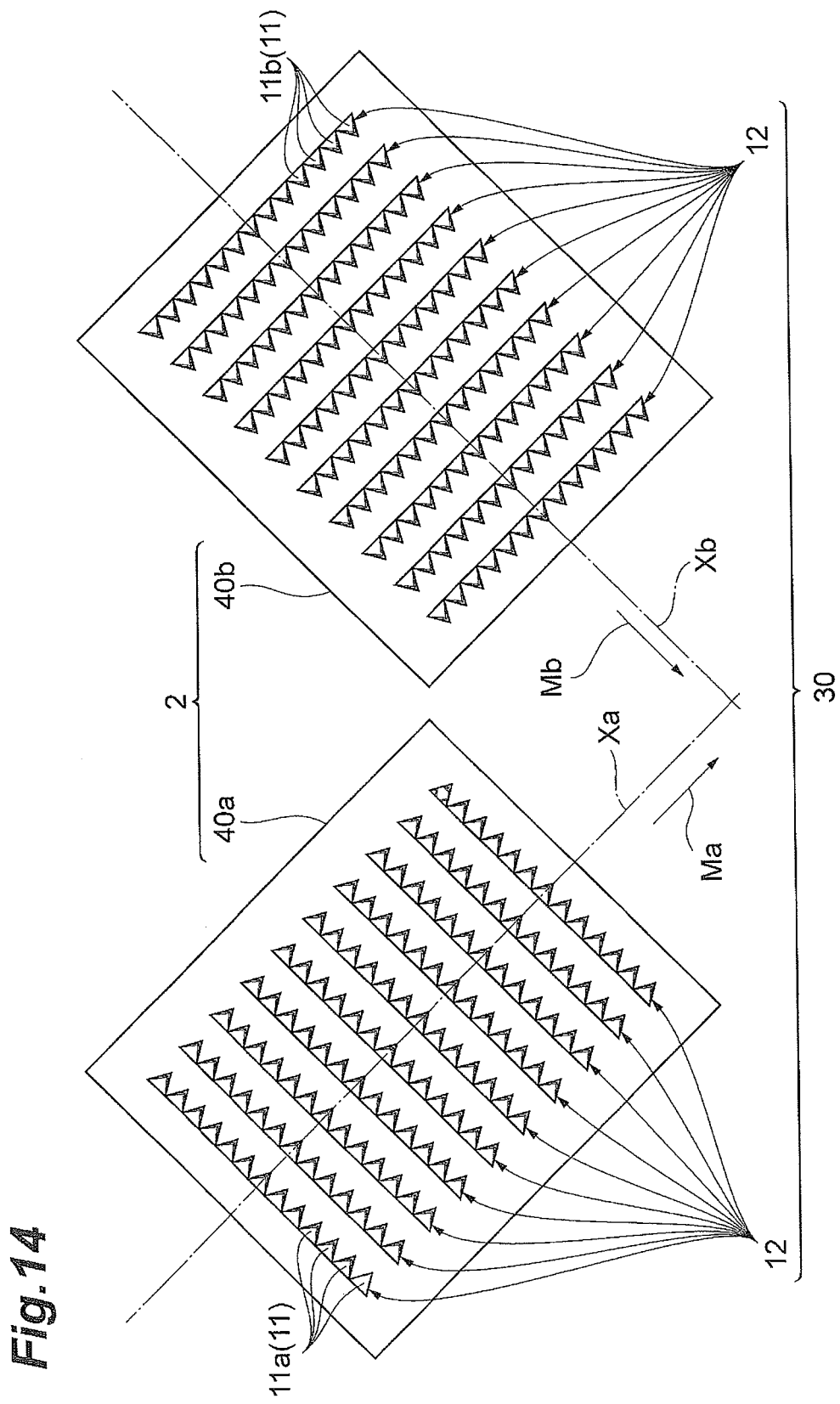
FIG. 14 is a plan view of yet another aspect of the microneedle device in accordance with the second embodiment.

Even in an example shown in FIG. 14, the sheets 40a and 40b are arranged so that the movement axis Xa of the sheet 40a and the movement axis Xb of the sheet 40b intersect each other. An angle between the two movement axes Xa and Xb is more than 0° and less than 180°. In this example, the two sheets 40a and 40b are moved so that the sheet 40a and the sheet 40b approach each other.

Figure 15:
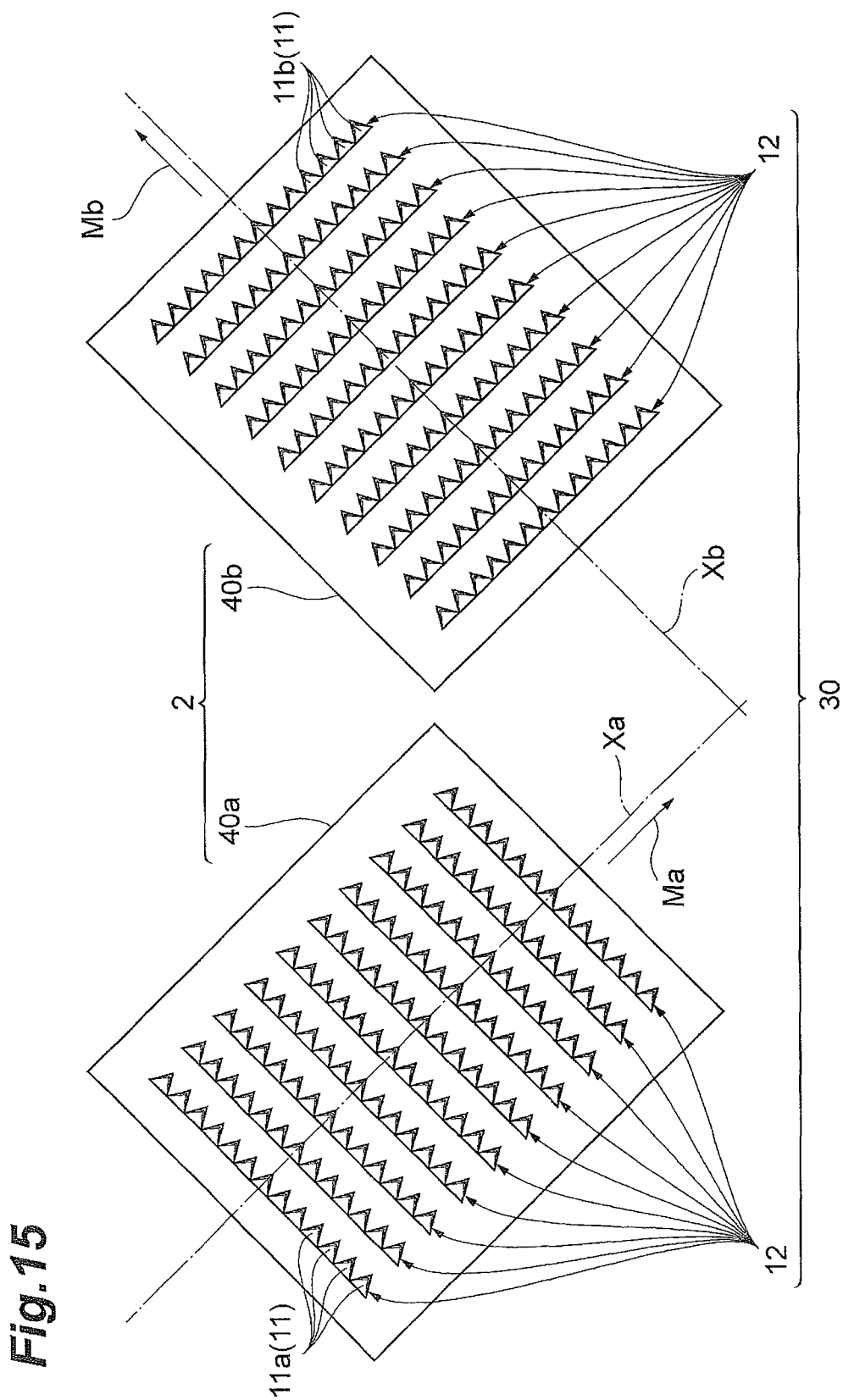
FIG. 15 is a plan view of yet another aspect of the microneedle device in accordance with the second embodiment.

Even in an example shown in FIG. 15, the sheets 40a and 40b are arranged so that the movement axis Xa of the sheet 40a and the movement axis Xb of the sheet 40b intersect each other. An angle between the movement axis Xa of the sheet 40a and the movement axis Xb of the sheet 40b is more than 0° and less than 180°. In this example, the sheet 40a is moved so as to approach an initial position of the sheet 40b, and the sheet 40b is moved so as to move away from an initial position of the sheet 40a.

In the examples of FIGS. 11 to 15, although the two sheets 40a and 40b are moved parallel to themselves, a movement method of the sheets is not limited to this way. For example, while one of the sheets is subjected to parallel movement, the other of the sheets may be moved along an arc. Alternatively, both of the sheets may be moved so that each of them moves along an arc.

The microneedle device 2 may be composed of only the two sheets 40a and 40b that are provided while separated from each other, and that are arranged as shown in FIGS. 11 to 15 when used. As shown in FIGS. 12 and 14, in a case where the two sheets 40a and 40b are arranged in juxtaposition to each other in a direction orthogonal to a tip direction of the microneedles 11, the microneedle device 2 may be composed of the two sheets 40a and 40b that are fitted to each other so as to be able to slide. Alternatively, the microneedle device 2 may comprise any support member (such as a rail for allowing the sheets 40a and 40b to slide) that supports the two sheets 40a and 40b arranged and moved as shown in any one of FIGS. 11 to 15.

Next, with reference to FIGS. 16 and 17, a method of use of the microneedle device 2 will be described. Hereinafter, an example in which a user oneself moves the microneedle device 2 shown in FIG. 11 with one's finger will be described.

Figure 16:
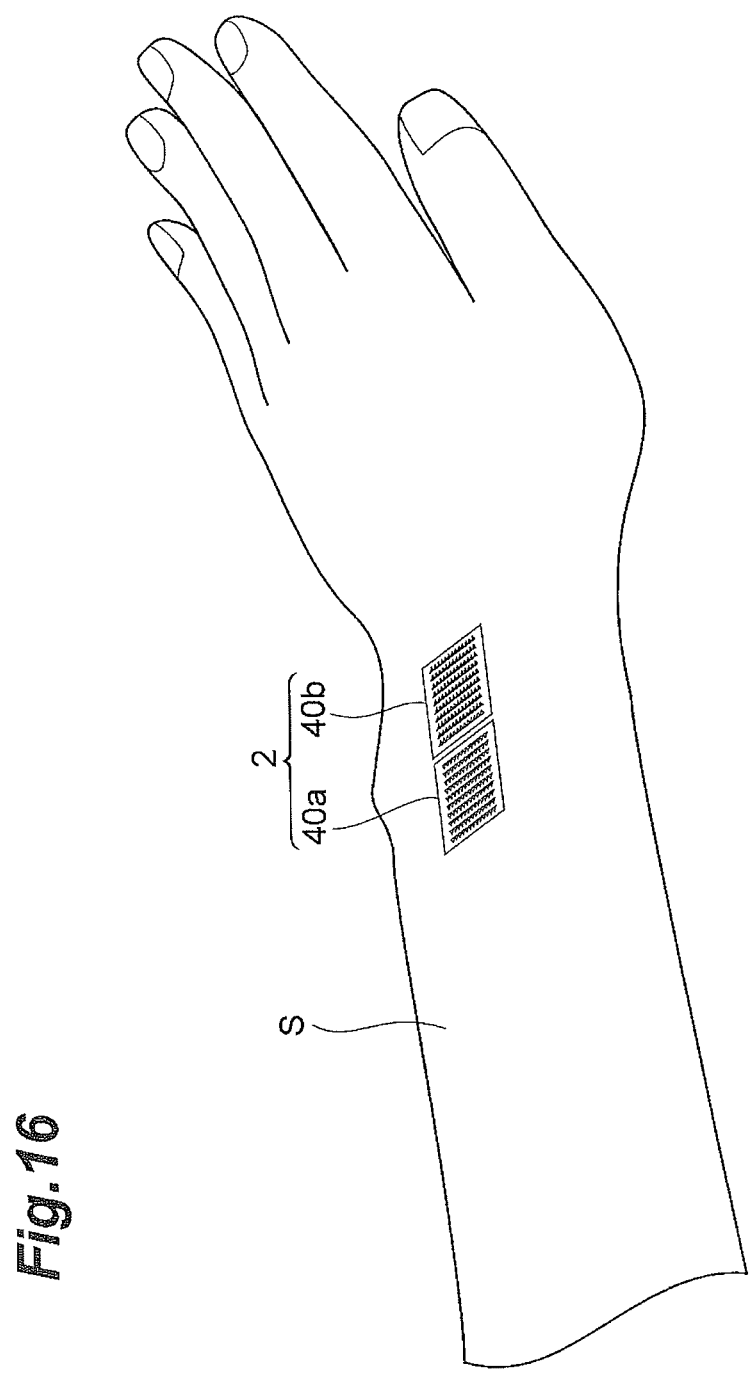
FIG. 16 shows a state where the microneedle device are placed on skin.

First, as shown in FIG. 16, while pointing the principal face (a face from which the microneedles 11 protrude) of the two sheets 40a and 40b to the skin S, the user places the microneedle device 2 on the skin to bring a tip of each of the microneedles 11 into contact with the skin S.

Figure 17:
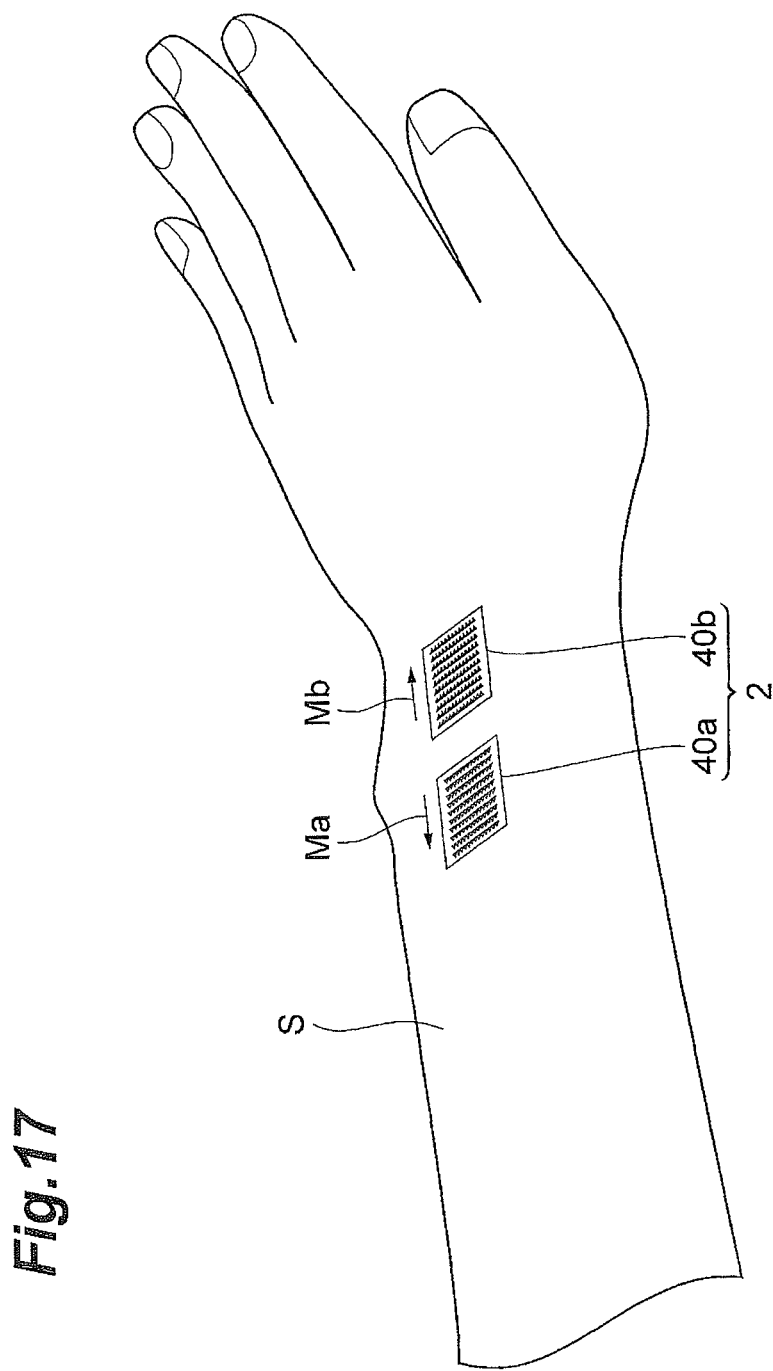
FIG. 17 shows a case of moving the microneedle device placed on the skin parallel to itself.

Subsequently, as shown in FIG. 17, while pressing a back face of each of the sheets 40a and 40b and moving the sheet 40a in the direction Ma and the sheet 40b in the direction Mb, along a surface of the skin S, the user presses the two sheets 40a and 40b into the skin S. At this time, the two sheets 40a and 40b move away from each other. By means of the parallel movement and the pressing, each of the microneedles 11 is stuck into the skin S while deforming the skin S near a contact point.

Even the present embodiment can get an effect as with the first embodiment above. Specifically, since each of the microneedles 11a and 11b, pointing a different direction from each other, is moved along its tip direction, each of the microneedles 11 is stuck into skin while deforming the skin. In this way, since the microneedles 11 themselves deform the skin, another member or mechanism for achieving the deformation is unnecessary, whereby it is possible to reduce a puncture device in size accordingly.

However, in order to perform puncture with the microneedle arrays independent of each other such as the second embodiment (refer to FIG. 11 and so on), a distance for allowing each of the microneedle arrays to be moved on skin is required. In contrast, the microneedle array of the first embodiment (FIG. 1) only turns on skin, so that an additional space for movement is unnecessary. That is, the microneedle array (a torsion type microneedle array) of the first embodiment is further suitable for downsizing. In addition, as compared with the microneedle array of the second embodiment, the microneedle array of the first embodiment is allowed to be punctured with even less force.

The present invention has been described in detail on the basis of its embodiments. However, the present invention is not limited to the embodiments above. The present invention may include various variations within a range without departing from the essence of the present invention.

Figure 18:
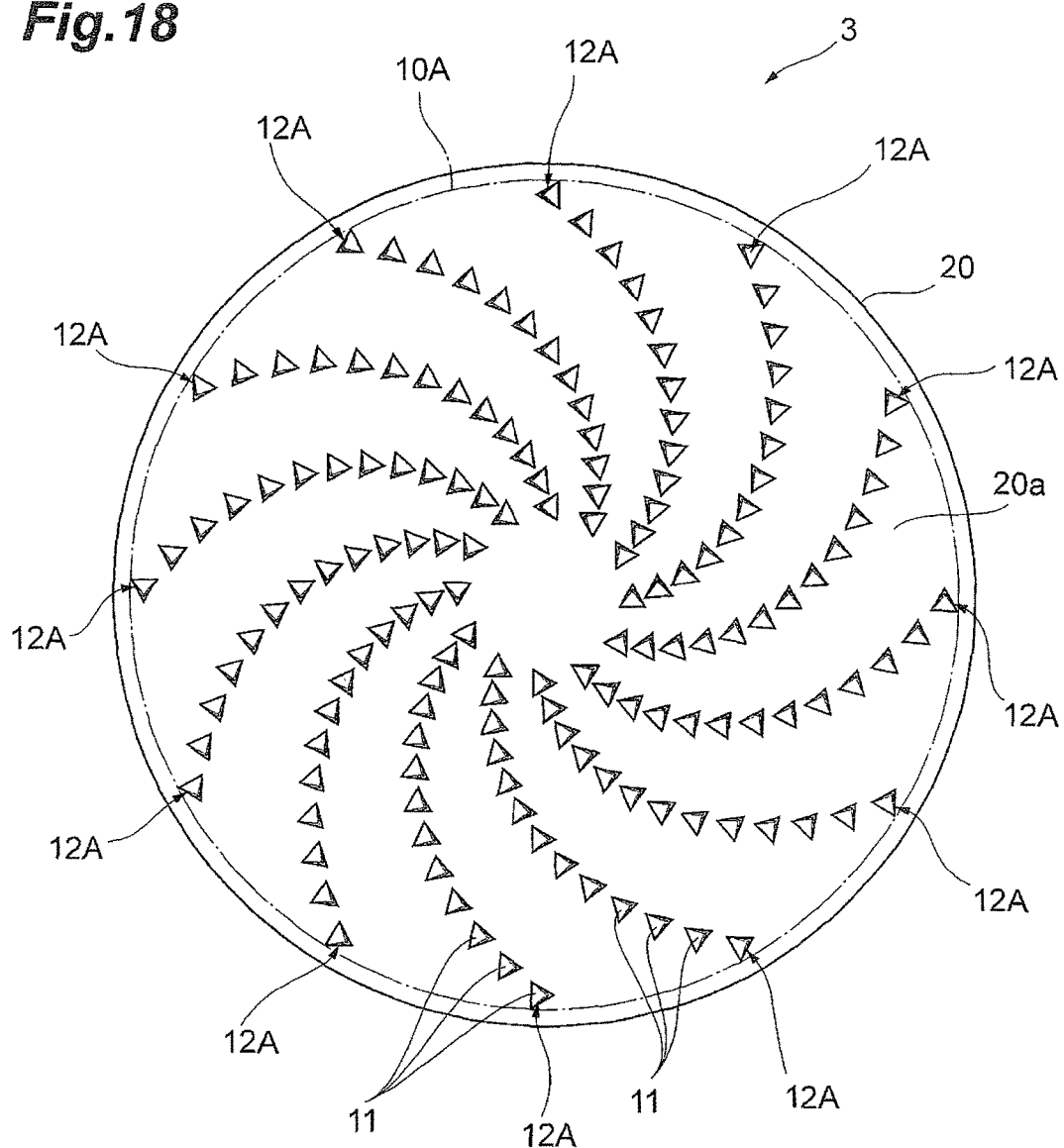
FIG. 18 is a plan view of a microneedle device in accordance with a variation.

With respect to each of the embodiments above, a shape of the line of the microneedles 11 is not limited to a linear shape, and may be optionally determined. For example, in a microneedle device 3 (a microneedle array 10A) shown in FIG. 18, a plurality of lines 12A extends radially from near the center of the sheet 20 as well as each of the lines 12A is formed in an arc shape. In the example of FIG. 18, each arc is convex in a clockwise direction.

Figure 19:
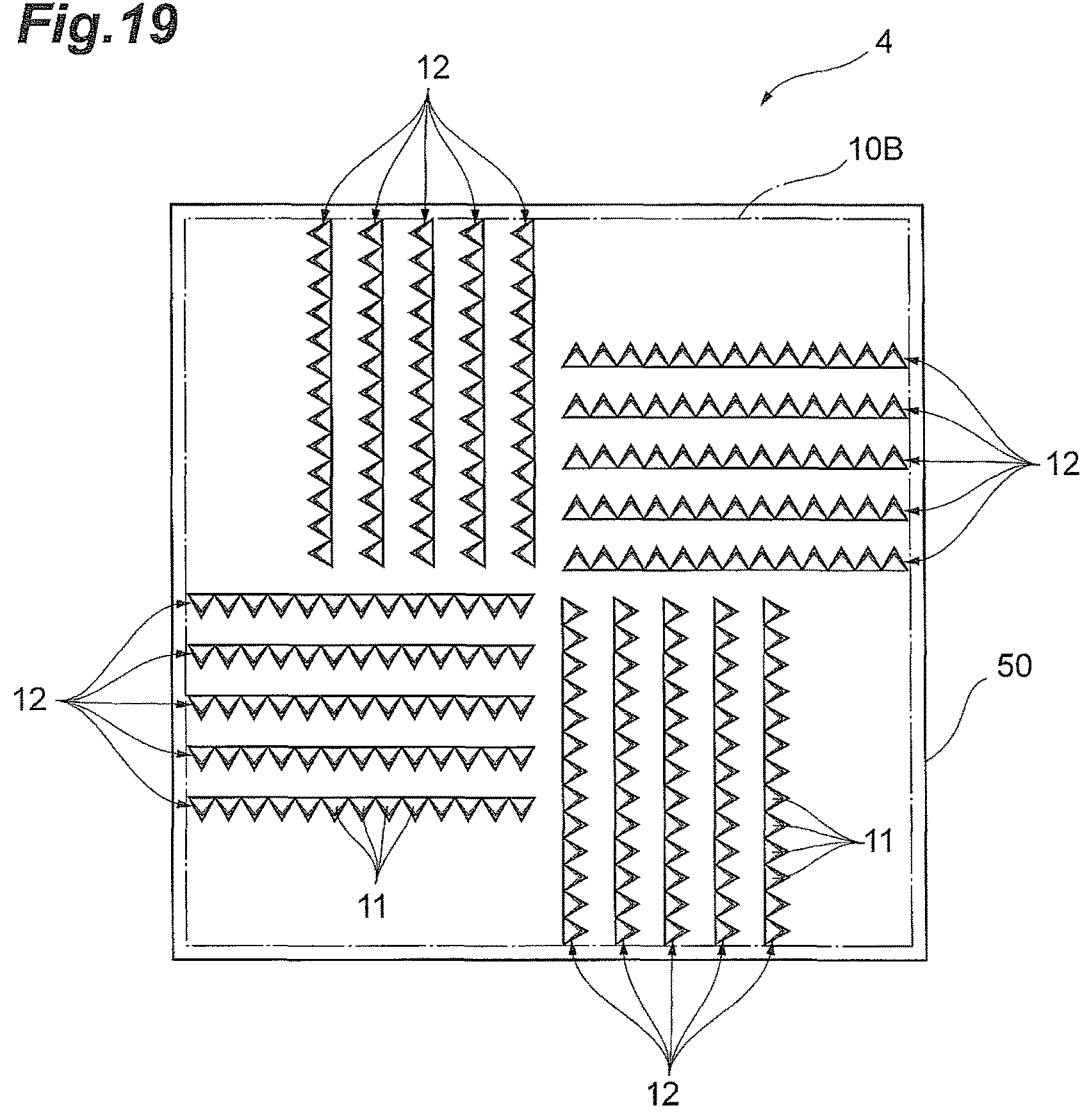
FIG. 19 is a plan view of a microneedle device in accordance with another variation.

With respect to each of the embodiments above, a shape of the sheet is not limited to a circle and a rectangle, may be any shape such as a square, a star, an ellipse, and another polygon. An aspect of the microneedle array (arrangement of the microneedles 11) can be optionally determined depending on a shape of the sheet. For example, a microneedle device 4 shown in FIG. 19 is formed by using a square sheet 50. In the example, if some lines 12 in which a tip direction of the microneedles 11 is the same are indicated as one group, it can be said that a microneedle array 10B is a set of four groups whose tip directions are different from each other by 90°. In FIG. 19, although the microneedle array 10B points in a counterclockwise direction as a whole, the direction may be clockwise. A difference in a tip direction of each group is not limited to 90°, and may be set at any angle.

Even in the microneedle devices 3 and 4 of a torsion type, both of a length and an inclination angle of the microneedle 11 may not be uniform, and the length or the inclination angle of each of the microneedles 11 may be different from each other as with the first embodiment.

In the second embodiment above, although the microneedle array 30 is composed of the microneedles 11 in two sheets, the microneedle array may be composed of microneedles in three or more sheets.

Figure 20:
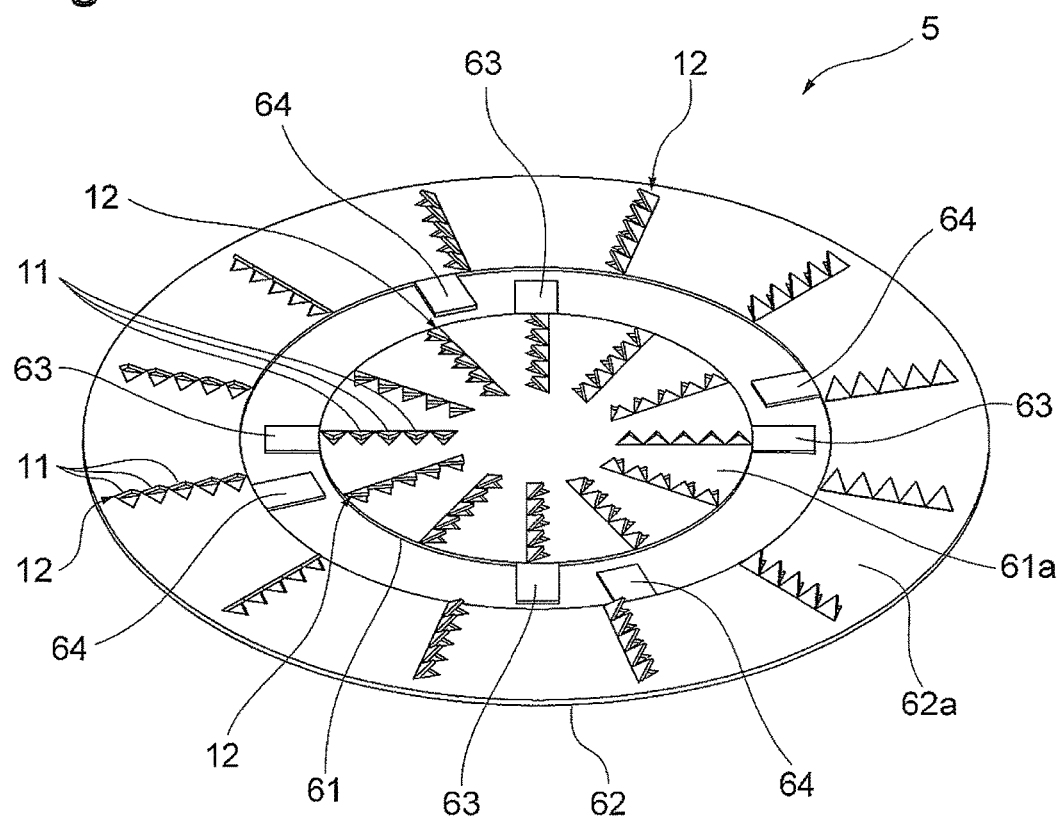
FIG. 20 is a perspective view of a microneedle device in accordance with yet another variation.

A microneedle array such as shown in FIG. 20 is also one aspect of the present invention. The microneedle array is a part of a microneedle device 5.

The microneedle device 5 comprises a set of a circular inner sheet 61 and ring-shaped (donut-shaped) outer sheet 62. Thus, a principal face (first support face) 61a of the inner sheet 61 and a principal face (second support face) 62a of the outer sheet 62 are independent of each other. Since an inner diameter of the outer sheet 62 is larger than an outer diameter of the inner sheet 61, it is possible to fit the inner sheet 61 inside the outer sheet 62. In an outer periphery portion of the inner sheet 61, there is provided a plurality of protrusions 63 extending radially outward. In an inner periphery portion of the outer sheet 62, there is provided a plurality of protrusions 64 extending radially inward. One protrusion 64 corresponds to one protrusion 63. When the microneedle device 5 is used, ones of the protrusions 63 and 64 is required to be brought into contact with the other of them, whereby the protrusions 63 and 64 may be thicker than the sheets 61 and 62. In an example of FIG. 20, although each of the four protrusions 63 and 64 is provided along a circumferential direction every 90°, the number of protrusions 63 and 64, and an installation interval thereof, are not limited to that. For example, each of three protrusions 63 and 64 may be provided every 120°, or each of six protrusions 63 and 64 may be provided every 60°.

Each of the inner sheet 61 and the outer sheet 62 comprises a large number of microneedles 11 formed by a method as with the first embodiment. A microneedle array in the microneedle device 5 is a set of the plurality of microneedles 11 on the inner sheet 61 and the plurality of microneedles 11 on the outer sheet 62. In both of the inner sheet 61 and the outer sheet 62, the plurality of microneedles 11 is arranged as with the first embodiment above. That is, in each of the sheets 61 and 62, each of the lines 12 that is a set of the microneedles 11 extends radially, and directions in which all of the microneedles 11 in both of the sheets 61 and 62 point are unified into a clockwise or counterclockwise direction. As with the first embodiment, an angle between two lines adjacent to each other may be optionally set. A length and an inclination angle of each of the microneedles 11 may not be uniform, and the length or the inclination angle of each of the microneedles 11 may be different from each other as with the first embodiment.

When the microneedle device 5 is used, a user first places the microneedle device 5 on the skin while pointing principal faces (support faces) 61a and 62a from which the microneedles 11 protrude to skin. At the time, with reference to a turning direction of the sheets 61 and 62 (a direction in which the microneedles 11 point), the sheets 61 and 62 are required to be placed on the skin so that the protrusion 64 is positioned in front of the protrusion 63 in each set of the protrusions 63 and 64 as well as the two protrusions 63 and 64 are away from each other.

Subsequently, the user turns the inner sheet 61 while pressing it toward the skin. By means of this operation, each of the microneedles 11 on the inner sheet 61 is stuck into the skin while deforming the skin. In addition, the protrusions 63 provided in the inner sheet 61 are brought into contact with the respective protrusions 64 to push the protrusions 64 along a turning direction, whereby the outer sheet 62 is also turned. As a result, each of the microneedles 11 on the outer sheet 62 is stuck into the skin while deforming the skin. In this way, in a case where the microneedle device 5 is used, after the microneedles on the inner sheet 61 (the microneedles positioned on the first support face) 11 start to turn, the microneedles on the outer sheet 62 (the microneedles positioned in the second support face positioned outside the first support face) 11 start to turn. In the each set, an initial gap between the protrusions 63 and 64 is set so that this kind of puncture can be achieved.

In a case where such the microneedle device 5 is used, it is possible to reliably stick the microneedles positioned on a center side of the device into skin.

Even in the microneedle device 5, each line of the microneedles may be formed in an arc shape as with the microneedle device 3.

The principal face (support face) from which the microneedles protrude may be convex, and a microneedle array including such a structure is also one aspect of the present invention. Here, the term "the support face is convex" means that a central portion of the support face rises. Although this definition includes an aspect in which the support face is a side face of a cone and an aspect in which the support face is a hemisphere face, an aspect in which the support face is convex is not limited to the aspects above. In addition, parameters defining a convex are not limited, and a center angle of a cone and a curvature of a hemisphere, for example, may be optionally determined.

Figure 21:
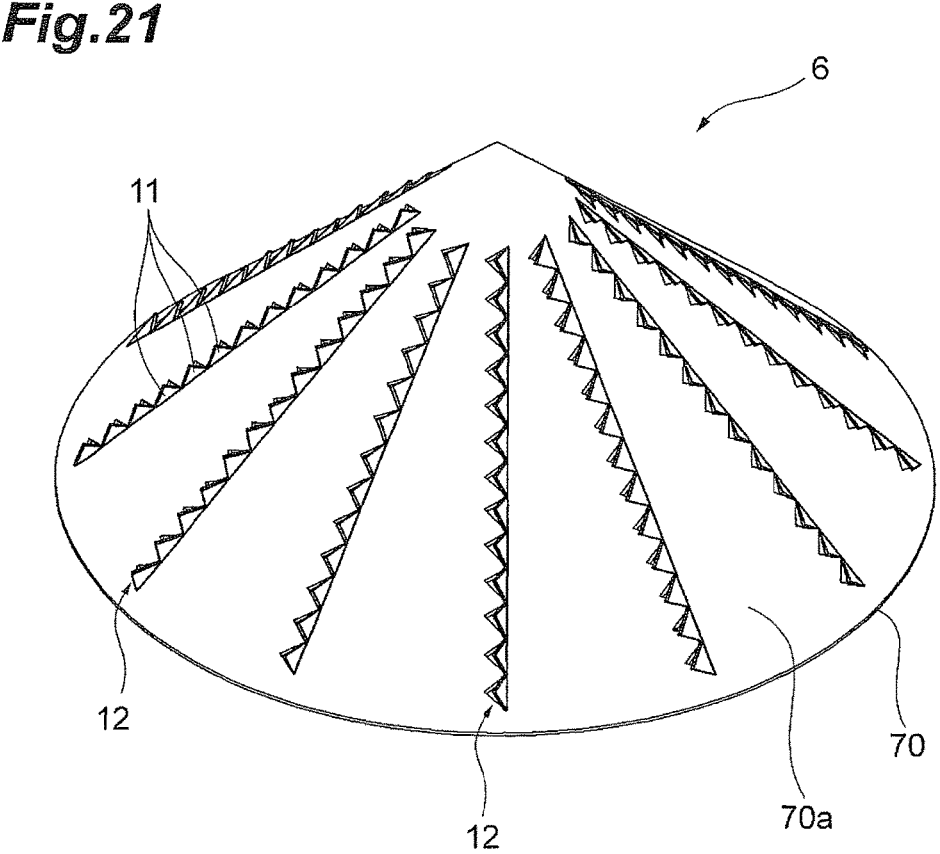
FIG. 21 is a perspective view of a microneedle device in accordance with yet another variation.

FIG. 21 shows an example in which a support face is convex. A microneedle array shown in FIG. 21 is a part of a microneedle device 6.

The microneedle device 6 can be acquired by forming a large number of microneedles 11 on a sheet 70 in a corn shape. Thus, a principal face (support face) 70a from which the microneedles 11 protrude is a side face of a cone. It is possible to form the microneedles 11 by a method as with the first embodiment. A microneedle array in the microneedle device 6 is a set of a plurality of lines 12 each of which extends along a generatrix of the sheet 70. Each of the lines 12 is composed of the plurality of microneedles 11. Directions in which all of the microneedles 11 point are unified into a clockwise or counterclockwise direction. An angle between two lines adjacent to each other may be optionally set. A length and an inclination angle of each of the microneedles 11 may not be uniform, and the length or the inclination angle of each of the microneedles 11 may be different from each other as with the first embodiment.

When the microneedle device 6 is used, a user first places the microneedle device 6 on skin while pointing the principal face 70a to the skin. Subsequently, the user presses the microneedle device 6 into the skin while turning the microneedle device 6 in a direction in which a tip of the microneedle 11 points. By means of this operation, each of the microneedles 11 is stuck into the skin while deforming the skin.

Even in the microneedle device 6, each line of the microneedles may be formed in an arc shape as with the microneedle device 3.

Although the microneedle is formed in a triangular shape in each of the embodiments above, a shape of the microneedle is not limited if capable of puncture. In addition, the microneedle may not be a planar shape that can be acquired by cutting out a sheet, and may be a three-dimensional shape such as a cone and a pyramid.

In each of the embodiments above, although the microneedle array is supported by a sheet-like member, the microneedle array may be formed on any face.

REFERENCE SIGNS LIST 1 to 6 . . . microneedle device, 10, 10A, 10B, 30 . . . microneedle array, 11, 11a, 11b . . . microneedle, 12, 12A . . . line of microneedles, 20, 40a, 40b, 50, 70 . . . sheet, 61 . . . inner sheet, 62 . . . outer sheet, 20a, 61a, 62a, 70a . . . principal face (support face), 20b . . . back face.

The invention claimed is:

1. A microneedle array comprising
a first line composed of a plurality of first microneedles that are inclined with respect to a support face; and
a second line composed of a plurality of second microneedles that are inclined with respect to the support face, wherein
the first line and the second line extend radially, and wherein
directions in which both the plurality of the first microneedles and the plurality of the second microneedles point are unified into a clockwise direction or a counterclockwise direction, and wherein
tips of the plurality of the first microneedles point in a first direction and tips of the plurality of the second microneedles point in a second direction different from the first direction, and wherein
the first microneedles in contact with skin is stuck into the skin while rotationally moving in the first direction along a surface of the skin, and the second microneedles in contact with the skin is stuck into the skin while rotationally moving in the second direction along the surface of the skin.

2. The microneedle array according to claim 1, wherein each of the first line and the second line is arranged along an arc.

3. The microneedle array according to claim 1, wherein at least one of the plurality of first or second microneedles positioned in a center portion of the support face is longer than at least one of the plurality of first or second microneedles positioned in a peripheral portion of the support face.

4. The microneedle array according to claim 1, wherein at least one of the plurality of first or second microneedles positioned in the center portion of the support face is shorter than at least one of the plurality of first or second microneedles positioned in the peripheral portion of the support face.

5. The microneedle array according to claim 1, wherein an inclination angle of at least one of the plurality of first or second microneedles positioned in the center portion of the support face is larger than an inclination angle of at least one of the plurality of first or second microneedles positioned in the peripheral portion of the support face.

6. The microneedle array according to claim 1, wherein
the support face includes a first support face and a second support face positioned outside the first support face, and
after at least one of the plurality of first or second microneedles positioned in the first support face starts to be rotationally moved, at least one of the plurality of first or second microneedles positioned in the second support face starts to be rotationally moved.

7. The microneedle array according to claim 1, wherein the support face is convex.

* * * * *